(12) United States Patent
Obermiller et al.

(10) Patent No.: US 8,906,083 B2
(45) Date of Patent: Dec. 9, 2014

(54) STENT VALVES AND USES OF SAME

(75) Inventors: Joseph F. Obermiller, West Lafayette, IN (US); Francisco Jose Osse, Sao Paulo (BR); Patricia E. Thorpe, Omaha, NE (US)

(73) Assignee: Cook Biotech Incorporated, West Lafayette, IN (US)

( * ) Notice: Subject to any disclaimer, the term of this patent is extended or adjusted under 35 U.S.C. 154(b) by 934 days.

(21) Appl. No.: 10/457,148

(22) Filed: Jun. 9, 2003

(65) Prior Publication Data
US 2004/0049262 A1 Mar. 11, 2004

Related U.S. Application Data

(63) Continuation of application No. 10/182,970, filed as application No. PCT/US01/03095 on Jan. 31, 2001, now abandoned.

(60) Provisional application No. 60/179,195, filed on Jan. 31, 2000.

(51) Int. Cl.
*A61F 2/06* (2013.01)
*A61F 2/24* (2006.01)

(52) U.S. Cl.
CPC .............. *A61F 2/2418* (2013.01); *A61F 2/2475* (2013.01)
USPC ......................................... 623/1.24; 623/2.18

(58) Field of Classification Search
CPC ....... A61F 2/24; A61F 2/2412; A61F 2/2418; A61F 2/2469; A61F 2/2475
USPC ........... 623/2.14–2.19, 1.15, 1.24–1.26, 2.13, 623/2.1–2.12
See application file for complete search history.

(56) References Cited

U.S. PATENT DOCUMENTS

| 3,755,823 | A |   | 9/1973  | Hancock |         |
|-----------|---|---|---------|---------|---------|
| 4,172,295 | A | * | 10/1979 | Batten  | 623/2.15 |
| 4,218,782 | A |   | 8/1980  | Rygg    |         |
| 4,222,126 | A | * | 9/1980  | Boretos et al. | 623/2.19 |
| 4,441,216 | A |   | 4/1984  | Ionescu et al. |     |

(Continued)

FOREIGN PATENT DOCUMENTS

| AU | 784782   | 9/2006 |
| DE | 19904975 | 9/2000 |

(Continued)

OTHER PUBLICATIONS

Gomez-Jorge, et al., "Percutaneous Deployment of a Valved Bovine Jugular Vein in the Swine Venous System: A Potential Treatment for Venous Insufficiency". *Journal of Vascular and Interventional Radiology*, Jul. 2000. vol. 11, No. 7. pp. 931-936.

(Continued)

*Primary Examiner* — Darwin Erezo
*Assistant Examiner* — Lindsey Bachman
(74) *Attorney, Agent, or Firm* — Woodard, Emhardt, Moriarty, McNett & Henry LLP

(57) ABSTRACT

The invention includes a medical device and more specifically relates to a valve found generally within a frame. In a preferred device, the frame preferably comprises a self-expanding stent frame, and the valve has at least one expandable and contractible pocket member within the stent frame for resisting and permitting fluid flow, respectively.

12 Claims, 12 Drawing Sheets

(56) References Cited

U.S. PATENT DOCUMENTS

| | | | |
|---|---|---|---|
| 4,580,568 A | | 4/1986 | Gianturco |
| 4,692,164 A | * | 9/1987 | Dzemeshkevich et al. .... 623/2.14 |
| 4,759,758 A | | 7/1988 | Gabbay |
| 4,851,000 A | * | 7/1989 | Gupta ........................ 623/2.18 |
| 4,851,001 A | | 7/1989 | Taheri |
| 4,902,508 A | | 2/1990 | Badylak et al. |
| 4,904,254 A | | 2/1990 | Lane |
| 5,147,389 A | | 9/1992 | Lane |
| 5,156,620 A | | 10/1992 | Pigott |
| 5,163,953 A | | 11/1992 | Vince |
| 5,258,023 A | | 11/1993 | Reger |
| 5,358,518 A | | 10/1994 | Camilli |
| 5,397,351 A | * | 3/1995 | Pavcnik et al. .............. 623/2.35 |
| 5,411,552 A | * | 5/1995 | Andersen et al. ............ 623/2.18 |
| 5,449,384 A | | 9/1995 | Johnson |
| 5,469,868 A | | 11/1995 | Reger |
| 5,480,424 A | * | 1/1996 | Cox ............................ 623/2.15 |
| 5,489,297 A | | 2/1996 | Duran |
| 5,500,014 A | | 3/1996 | Quijano et al. |
| 5,545,214 A | | 8/1996 | Stevens |
| 5,554,185 A | | 9/1996 | Block |
| 5,554,389 A | | 9/1996 | Badylak et al. |
| 5,595,571 A | | 1/1997 | Jaffe et al. |
| 5,607,465 A | | 3/1997 | Camilli |
| 5,609,598 A | | 3/1997 | Laufer et al. |
| 5,609,626 A | | 3/1997 | Quijano et al. |
| 5,665,103 A | | 9/1997 | Lafontaine et al. |
| 5,711,969 A | | 1/1998 | Patel et al. |
| 5,720,777 A | | 2/1998 | Jaffe et al. |
| 5,733,337 A | | 3/1998 | Carr et al. |
| 5,800,522 A | | 9/1998 | Campbell et al. |
| 5,810,847 A | | 9/1998 | Laufer et al. |
| 5,824,061 A | | 10/1998 | Quijano et al. |
| 5,843,171 A | | 12/1998 | Campbell et al. |
| 5,843,180 A | | 12/1998 | Jaffe et al. |
| 5,843,181 A | | 12/1998 | Jaffe et al. |
| 5,855,597 A | | 1/1999 | Jayaraman |
| 5,855,601 A | | 1/1999 | Chuter et al. |
| 5,861,028 A | * | 1/1999 | Angell .......................... 623/2.11 |
| 5,876,445 A | | 3/1999 | Andersen et al. |
| 5,885,619 A | | 3/1999 | Patel et al. |
| 5,935,163 A | * | 8/1999 | Gabbay ........................ 623/2.14 |
| 5,955,110 A | | 9/1999 | Patel et al. |
| 5,957,949 A | | 9/1999 | Leonhardt et al. |
| 5,968,096 A | | 10/1999 | Whitson et al. |
| 6,015,431 A | | 1/2000 | Thornton et al. |
| 6,110,201 A | | 8/2000 | Quijano et al. |
| 6,126,686 A | | 10/2000 | Badylak et al. |
| 6,168,614 B1 | | 1/2001 | Andersen et al. |
| 6,200,336 B1 | | 3/2001 | Pavcnik et al. |
| 6,287,334 B1 | * | 9/2001 | Moll et al. ................... 623/1.24 |
| 6,299,637 B1 | | 10/2001 | Shaolian et al. |
| 6,425,916 B1 | | 7/2002 | Garrison et al. |
| 6,458,153 B1 | * | 10/2002 | Bailey et al. ................. 623/1.24 |
| 6,508,833 B2 | | 1/2003 | Pavcnik et al. |
| 6,558,418 B2 | * | 5/2003 | Carpentier et al. .......... 623/2.14 |
| 6,582,462 B1 | | 6/2003 | Andersen et al. |
| 6,716,241 B2 | | 4/2004 | Wilder et al. |
| 6,752,828 B2 | | 6/2004 | Thornton |
| 6,908,481 B2 | | 6/2005 | Cribler |
| 2001/0007956 A1 | | 7/2001 | Letac et al. |
| 2001/0011187 A1 | | 8/2001 | Pavcnik et al. |
| 2001/0039450 A1 | | 11/2001 | Pavcnik et al. |
| 2002/0123800 A1 | | 9/2002 | Taheri |
| 2002/0188348 A1 | | 12/2002 | DiMatteo et al. |
| 2003/0036795 A1 | | 2/2003 | Andersen et al. |
| 2003/0130726 A1 | | 7/2003 | Thorpe et al. |
| 2003/0191525 A1 | | 10/2003 | Thornton |
| 2003/0208261 A1 | | 11/2003 | Thorpe et al. |
| 2004/0015230 A1 | | 1/2004 | Moll et al. |
| 2004/0049262 A1 | | 3/2004 | Obermiller et al. |
| 2004/0193253 A1 | | 9/2004 | Thorpe et al. |
| 2005/0049696 A1 | | 3/2005 | Siess |

FOREIGN PATENT DOCUMENTS

| | | |
|---|---|---|
| EP | 0 808 614 A | 11/1997 |
| EP | 0 850 607 A | 7/1998 |
| EP | 0856300 | 8/1998 |
| EP | 1 057 460 A | 12/2000 |
| EP | 1255510 | 4/2007 |
| EP | 1255510 B3 | 3/2009 |
| WO | WO 91/17720 | 11/1991 |
| WO | WO 93/16593 | 8/1993 |
| WO | WO 98/22158 | 5/1998 |
| WO | WO 98/25549 | 6/1998 |
| WO | WO 98/25636 | 6/1998 |
| WO | WO 98/25637 | 6/1998 |
| WO | WO 98/26291 | 6/1998 |
| WO | WO 98/27895 | 7/1998 |
| WO | WO 98/29057 | 7/1998 |
| WO | WO 99/15224 | 4/1999 |
| WO | WO 99/62431 | 12/1999 |
| WO | WO 00/42950 | 7/2000 |
| WO | WO 00/47136 | 8/2000 |
| WO | WO 01/19285 | 3/2001 |
| WO | WO 01/49213 | 7/2001 |
| WO | WO 01/54625 | 8/2001 |
| WO | WO 01/56500 | 8/2001 |
| WO | WO 03/070124 | 8/2003 |

OTHER PUBLICATIONS

Guyton, *Textbook of Medial Physiology*, 8$^{th}$ Edition. 1991. pp. 166-167. W.B. Saunders Co., Philadelphia, PA.

Huynh, et al., "Remodeling of an Acellular Collagen Graft into a Physiologically Responsive Neovesser". *Nature Biotechnology*, Nov. 1999. vol. 17, No. 11. pp. 1083-1086.

Love, J. W. "Chapter 1: Early Experience with Autologous Tissue Heart Valves", *Autologous Tissue Heart Valves*, Jan. 1993. pp. 1-22. Landes Bioscience.

Ofenloch, J. et al., "Endoscopic Venous Valve Transplantation with a Valve-Stent Device". *Annals of Vascular Surgery*, Jan. 1997. vol. 11, No. 1. pp. 62-67. Springer-Verlag New York, Inc.

Uflacker, et al. "Percutaneously Introduced Artificial Venous Valve: Experimental Use in Pigs". *Radiology*, Nov. 1993. vol. 189 (P) Supplement, 79$^{th}$ Scientific Assembly and Annual Meeting; Abstract No. 54C. pp. 113-114.

Cook's Notice to Admit Facts, UK HC 08 CO 0934, dated May 30, 2008.

Cook's Reply and Counterclaim to Edwards' UK Complaint, dated May 9, 2008.

Cook's Response to Edwards' Notice to Admit Facts in UK Complaint, dated Jun. 20, 2008.

Edwards' Complaint filed in United Kingdom No. HC 08 CO 0934, dated Apr. 2, 2008.

Edwards' Notice to Admit Facts in UK Complaint, dated May 29, 2008.

Edwards' Response to Notice to Admit Facts, UK HC 08 CO 0934, dated Jun. 20, 2008.

English Translation of Complaint filed in Germany, Docket No. 4b O 19/08, filed Feb. 1, 2008, 30 pages.

Exhibit 1, Particulars of Claim of Edwards' UK Complaint filed Apr. 2, 2008.

Exhibit 2 of Edwards' UK Complaint, Grounds of Invalidity, dated Apr. 2, 2008.

Office Action issued in U.S. Appl. No. 10/837,058, filed Apr. 30, 2004, dated Feb. 20, 2007.

Office Action issued in U.S. Appl. No. 10/837,058, filed Apr. 30, 2004, dated Jan. 16, 2008.

Office Action issued in U.S. Appl. No. 10/837,058, filed Apr. 30, 2004, dated May 4, 2006.

Office Action issued in U.S. Appl. No. 10/837,058, filed Apr. 30, 2004, dated Sep. 18, 2007.

"Aortic and venous valve for percutaneous insertion" by D. Pavcnik et al., published in 2000 in Min Invas Ther & Allied Technol 2000, vol. 9, pp. 287-292

(56) References Cited

OTHER PUBLICATIONS

Annex 1 to the Expert Reports of Dr. Nigel Buller, Curriculum Vitae of Dr. Nigel Pearson Buller, Edwards' United Kingdom action for Invalidity, Claim No. HC 08C00934.
Annex 1 to the Expert Reports of Dr. Rodolfo Quijano, Curriculum Vitae of Dr. Rodolfo Quijano, Edwards' United Kingdom action for Invalidity, Claim No. HC 08C00934.
Annex 10 to the Expert Reports of Dr. Nigel Buller, Patent 5035706 to Gianturco, Edwards' United Kingdom action for Invalidity, Claim No. HC 08C00934.
Annex 11 to the Expert Reports of Dr. Nigel Buller, p. 215 of Interventional Cardiology, 6th edition, Hogrefe & Huber (1989), Edwards' United Kingdom action for Invalidity, Claim No. HC 08C00934.
Annex 12 to the Expert Reports of Dr. Nigel Buller, Patent 3755823 to Hancock, Edwards' United Kingdom action for Invalidity, Claim No. HC 08C00934.
Annex 13 to the Expert Reports of Dr. Nigel Buller, GB 2056023A, Edwards' United Kingdom action for Invalidity, Claim No. HC 08C00934.
Annex 14 to the Expert Reports of Dr. Nigel Buller, Kocher et al., JVIR (1998) vol. 9, pp. 1007-1010, Edwards' United Kingdom action for Invalidity, Claim No. HC 08C00934.
Annex 15 to the Expert Reports of Dr. Nigel Buller, Davies et al., Cardiovascular and Interventional Radiology (2000) vol. 23, pp. 487-489, Edwards' United Kingdom action for Invalidity, Claim No. HC 08C00934.
Annex 16 to the Expert Reports of Dr. Nigel Buller, EP 0808614A, Edwards' United Kingdom action for Invalidity, Claim No. HC 08C00934.
Annex 17 to the Expert Reports of Dr. Nigel Buller, Carpentier-Edwards Peridardial Bioprosthesis, Edwards' United Kingdom action for Invalidity, Claim No. HC 08C00934.
Annex 2 to the Expert Reports of Dr. Nigel Buller, Chapter 15 of Overview of Cardiac Surgery for the Cardiologist, Springer-Verlag (1994), Edwards' United Kingdom action for Invalidity, Claim No. HC 08C00934.
Annex 3 to the Expert Reports of Dr. Nigel Buller, Chapters 2, 16, 17 and 18 of Interventional Cardiology, 6th edition, Hogrefe & Huber (1989), Edwards' United Kingdom action for Invalidity, Claim No. HC 08C00934.
Annex 4 to the Expert Reports of Dr. Nigel Buller, Pavcnik et al., Cardiovascular Radiology (Apr. 1992), pp. 151-154, Edwards' United Kingdom action for Invalidity, Claim No. HC 08C00934.
Annex 5 to the Expert Reports of Dr. Nigel Buller, Andersen et al., European Heart J. (1992) vol. 13, pp. 704-708, Edwards' United Kingdom action for Invalidity, Claim No. HC 08C00934.
Annex 6 to the Expert Reports of Dr. Nigel Buller, Knudsen et al., Artificial Heart and Cardiac Assist Devices (1993) 18(5), pp. 253-262, Edwards' United Kingdom action for Invalidity, Claim No. HC 08C00934.
Annex 7 to the Expert Reports of Dr. Nigel Buller, Andersen, Int. J. Angiology (1998) vol. 7, pp. 102-106, Edwards' United Kingdom action for Invalidity, Claim No. HC 08C00934.
Annex 8 to the Expert Reports of Dr. Nigel Buller, Chapter 75 of Textbook of Interventional Cardiology, 2nd edition (1994), Edwards' United Kingdom action for Invalidity, Claim No. HC 08C00934.
Annex 9 to the Expert Reports of Dr. Nigel Buller, Rosch et al., Cardiovascular and Interventional Radiology (1992) vol. 15, pp. 319-327, Edwards' United Kingdom action for Invalidity, Claim No. HC 08C00934.
Annex to the Expert Reports of Dr. Rodolfo Quijano, RCQ-1, Baxter Healthcare Carpentier-Edwards Pericardial Bioprosthesis Mini-Symposium, Chicago (Apr. 24, 1993), Edwards' United Kingdom action for Invalidity, Claim No. HC 08C00934.
Annex to the Expert Reports of Dr. Rodolfo Quijano, RCQ-2, USP 24 NF 19 US Pharmacopeia & National Formulary, Edwards' United Kingdom action for Invalidity, Claim No. HC 08C00934.
Cook Closing Skeleton Brief, Edwards' United Kingdom action for Invalidity, Claim No. HC 08C00934.
Cook Opening Skeleton Brief, redacted, Edwards' United Kingdom action for Invalidity, Claim No. HC 08C00934.
Edwards' Closing Skeleton Brief, Edwards' United Kingdom action for Invalidity, Claim No. HC 08C00934.
Edwards' Opening Skeleton Brief, redacted, Edwards' United Kingdom action for Invalidity, Claim No. HC 08C00934.
English translation of Cook's Brief due Feb. 6, 2009, Cook's German action for Patent Infringement, Docket No. 4b 019/08.
English translation of Cook's Brief filed Nov. 5, 2008, Cook's German action for Patent Infringement, Docket No. 4b 019/08.
English translation of Edwards' Brief due Feb. 5, 2009, Cook's German action for Patent Infringement, Docket No. 4b 019/08.
English translation of Edwards' Nullity Action re EP 1255510B1, Edwards' German Nullity action, Docket No. DE 60128069T2.
Exhibit NI30, Wernly et al., "Choosing a Prosthetic Heart Valve," Cardiology Clinics, vol. 16, pp. 491-504 (1998), Edwards' German Nullity action, Docket No. DE 60128069T2.
Exhibit NI31, "Prosthetic Heart Valve Performance: Long Term Follow-up," Curr Probl Cardiolo Jun. 1992, Edwards' German Nullity action, Docket No. DE 60128069T2.
Exhibit to the Expert Reports of Prof. David Williams, DFW-10, Current brochure from Edwards' website re Carpentier-Edwards bioprosthesis, Edwards' United Kingdom action for Invalidity, Claim No. HC 08C00934
Exhibit to the Expert Reports of Prof. David Williams, DFW-11, "A New Biomaterial Derived from Small Intestine Submucosa and developed into a Wound Matrix Device", Edwards' United Kingdom action for Invalidity, Claim No. HC 08C00934.
Exhibit to the Expert Reports of Prof. David Williams, DFW-12, "Mapping of Gluteraldehyde-treated Bovine Pericardium and tissue Selection for Bioprosthetic Heart Valves", Edwards' United Kingdom action for Invalidity, Claim No. HC 08C00934.
Exhibit to the Expert Reports of Prof. David Williams, DFW-2, Curriculum Vitae of Prof. David F. Williams, Edwards' United Kingdom action for Invalidity, Claim No. HC 08C00934.
Exhibit to the Expert Reports of Prof. David Williams, DFW-3, page from Medtronic website re Hancock II aortic and mitral bioprostheses, Edwards' United Kingdom action for Invalidity, Claim No. HC 08C00934.
Exhibit to the Expert Reports of Prof. David Williams, DFW-4, Rao et al., "Prosthetic mismatch affects survival after aortic valve repalcement," Circulation, vol. 102, Issue 19, pp. 1115-1119, (2002), Edwards' United Kingdom action for Invalidity, Claim No. HC 08C00934.
Exhibit to the Expert Reports of Prof. David Williams, DFW-5, Further page from Medtronic website re Hancock II aortic and mitral bioprostheses, Edwards' United Kingdom action for Invalidity, Claim No. HC 08C00934.
Exhibit to the Expert Reports of Prof. David Williams, DFW-6, US Patent 4580568 to Gianturco, Edwards' United Kingdom action for Invalidity, Claim No. HC 08C00934.
Exhibit to the Expert Reports of Prof. David Williams, DFW-7, Chapter 24, "The Applied VE Micro Stent" of Endoluminal Stenting (1996), Edwards' United Kingdom action for Invalidity, Claim No. HC 08C00934.
Exhibit to the Expert Reports of Prof. David Williams, DFW-8, US Patent 5035706 to Gianturco, Edwards' United Kingdom action for Invalidity, Claim No. HC 08C00934.
Exhibit to the Expert Reports of Prof. David Williams, DFW-9, Rosch et al. "Gianturco-Rosch Expandable Z-Stents in the Treatment of Superior Vena Cava Syndrome," Cardio Vascular and Interventional Radiology (1992) vol. 15, pp. 319-332, Edwards' United Kingdom action for Invalidity, Claim No. HC 08C00934.
Exhibit to the Expert Reports of Prof. David Williams, DFW-1, First witness Statement of Stanton Rowe from CoreValve proceedings, Edwards' United Kingdom action for Invalidity, Claim No. HC 08C00934.
Exhibit to the Expert Reports of Prof. Martin Rothman, MTR-1, Curriculum Vitae of Prof. Martin Rothman, Edwards' United Kingdom action for Invalidity, Claim No. HC 08C00934.
Exhibit to the Expert Reports of Prof. Martin Rothman, MTR10, Khambadkone et al., "Percutaneous Pulmonary Valve Implantation

(56) References Cited

OTHER PUBLICATIONS in Humans Results in 59 Consecutive Patients," Circulation (2005, Vo. 112, pp. 1189-1197, Edwards' United Kingdom action for Invalidity, Claim No. HC 08CO0934.

Exhibit to the Expert Reports of Prof. Martin Rothman, MTR-11, Cribier et al., "Percutaneous Transcatheter Implantation of an Aortic Valve Prosthesis for Calcific Aortic Stenosis: First Human Case Description," Circulation (2002) vol. 106, pp. 3006-3008, Edwards' United Kingdom action for Invalidity, Claim No. HC 08CO0934.

Exhibit to the Expert Reports of Prof. Martin Rothman, MTR-12, Boden et al., "Optimal Medical Therapy with or without PCI for Stable Coronary Disease," N Engl J Med (2007) vol. 356, pp. 1503-1516 (Apr. 12, 2007), published at www.nejm.org on Mar 26, 2007, Edwards' United Kingdom action for Invalidity, Claim No. HC 08CO0934.

Exhibit to the Expert Reports of Prof. Martin Rothman, MTR-13, US Patent 4580568 to Gianturco, Edwards' United Kingdom action for Invalidity, Claim No. HC 08CO0934.

Exhibit to the Expert Reports of Prof. Martin Rothman, MTR-14, Pages from Edwards' website, Edwards' United Kingdom action for Invalidity, Claim No. HC 08CO0934.

Exhibit to the Expert Reports of Prof. Martin Rothman, MTR-17, Prof. Martin Rothman's expert report in the CoreValve proceedings, dated Apr. 28, 2008, Edwards' United Kingdom action for Invalidity, Claim No. HC 08CO0934.

Exhibit to the Expert Reports of Prof. Martin Rothman, MTR-18, Contents pages of the Third Edition of the Textbook of Interventional Cardiology (1999), Edwards' United Kingdom action for Invalidity, Claim No. HC 08CO0934.

Exhibit to the Expert Reports of Prof. Martin Rothman, MTR-19, Stents listed in Table 1 of the Second Expert Report of Prof. Martin Rothman, Edwards' United Kingdom action for Invalidity, Claim No. HC 08CO0934.

Exhibit to the Expert Reports of Prof. Martin Rothman, MTR-2, Cribier et al., "Percutaneous Aortic Valves: Emerging", Indian Heart J 2007, Suppl B, pp. B111-B132, Edwards' United Kingdom action for Invalidity, Claim No. HC 08CO0934.

Exhibit to the Expert Reports of Prof. Martin Rothman, MTR-3, Andersen et al. "Transluminal implantation of artificial heart valves. Description of a new expandable aortic valve and initial results with implantation by catheter technique in closed chest pigs" European Heart Journal, 1992 vol. 13, pp. 704-708, Edwards' United Kingdom action for Invalidity, Claim No. HC 08CO0934.

Exhibit to the Expert Reports of Prof. Martin Rothman, MTR-4, Pavcnik et al., "Development and Initial Experimental Evaluation of a Prosthetic Aortic Valve for Transcatheter Placement," Radiology 1992, vol. 183, pp. 151-154, Edwards' United Kingdom action for Invalidity, Claim No. HC 08CO0934.

Exhibit to the Expert Reports of Prof. Martin Rothman, MTR-5, Sochman et al., "Percutaneous Transcatheter Aortic Disc Valve Prosthesis Implantation: A Feasibility Study", Cardiovasc Intervent Radiol (2000) vol. 23, pp. 384-388, Edwards' United Kingdom action for Invalidity, Claim No. HC 08CO0934

Exhibit to the Expert Reports of Prof. Martin Rothman, MTR-6, Bonhoeffer et al., "Transcathether Implantation of a Bovine Valve in Pulmonary Position: A Lamb Study," Circulation 2000, vol. 102, pp. 813-816, Edwards' United Kingdom action for Invalidity, Claim No. HC 08CO0934.

Exhibit to the Expert Reports of Prof. Martin Rothman, MTR-7, Bonhoeffer et al., "Percutaneous replacement of a pulmonary valve in a right-ventricle to pulmonary-artery prosthetic conduit with valve dysfunction," Lancet 2000, vol. 356, pp. 1403-1405, Edwards' United Kingdom action for Invalidity, Claim No. HC 08CO0934.

Ehibit to the Expert Reports of Prof. Martin Rothman, MTR-8, Noudjemline et al., "Percutaneous implantation of a vave in the descending aorta of lambs," European Heart Journal (2000) vol. 23, pp. 1045-1049, Edwards' United Kingdom action for Invalidity, Claim No. HC 08CO0934

Exhibit to the Expert Reports of Prof. Martin Rothman, MTR9, Lutter et al., "Percutaneous aortic valve replacement: An experimental study, Studies on implantation," J. Thorac Cardiovasc Surg (2002) vol. 123, pp. 768-776, Edwards' United Kingdom action for Invalidity, Claim No. HC 08CO0934.

Expert Report of Dr. Nigel Buller, dated Jan. 12, 2009, Edwards' United Kingdom action for Invalidity, Claim No. HC 08CO0934.

Expert Report of Dr. Nigel Buller, non-confidential annex—infringement, dated Jan. 12, 2009, Edwards' United Kingdom action for Invalidity, Claim No. HC 08CO0934.

Expert Report of Dr. Rodolfo Quijano, dated Jan. 9, 2009, Edwards' United Kingdom action for Invalidity, Claim No. HC 08CO0934.

First Expert Report of Prof. David Williams, dated Jan. 12, 2009, Edwards' United Kingdom action for Invalidity, Claim No. HC 08CO0934.

First Expert Report of Prof. Martin Rothman, dated Jan. 12, 2009, Edwards' United Kingdom action for Invalidity, Claim No. HC 08CO0934.

Fourth Expert Report of Prof. Martin Rothman, dated Apr. 22, 2009, Edwards' United Kingdom action for Invalidity, Claim No. HC 08CO0934.

Second Expert Report of Dr. Nigel Buller, dated Feb. 25, 2009, Edwards' United Kingdom action for Invalidity, Claim No. HC 08CO0934.

Second Expert Report of Dr. Rodolfo Quijano, dated Feb. 26, 2009, Edwards' United Kingdom action for Invalidity, Claim No. HC 08CO0934.

Second Expert Report of Prof. David Williams, dated Feb. 5, 2009, Edwards' United Kingdom action for Invalidity, Claim No. HC 08CO0934.

Second Expert Report of Prof. Martin Rothman, dated Feb. 5, 2009, Edwards' United Kingdom action for Invalidity, Claim No. HC 08CO0934.

Third Expert Report of Dr. Nigel Buller, dated Apr. 21, 2009, Edwards' United Kingdom action for Invalidity, Claim No. HC 08CO0934.

Third Expert Report of Dr. Rudolfo Quijano, dated Apr. 27, 2009, Edwards' United Kingdom action for Invalidity, Claim No. HC 08CO0934.

Third Expert Report of Prof. David Williams, dated Apr. 22, 2009, Edwards' United Kingdom action for Invalidity, Claim No. HC 08CO0934.

Third Expert Report of Prof. Martin Rothman, dated Apr. 3, 2009, Edwards' United Kingdom action for Invalidity, Claim No. HC 08CO0934.

Judgment in HC08 C 00934 Edwards v. Cook, Jun. 12, 2009.

Statement of Grounds and Particulars in Edwards' AU Opposition to AU 2006218278.

Translation of Complaint for Declaration of Nullity EP 1255510.

Amendment to claims in related EP Application No. 07008364.7, Sep. 27, 2010, 25 pages.

Submission by third party Edwards in related EP Application No. 07008364.7, Mar. 25, 2010, 19 pages.

\* cited by examiner

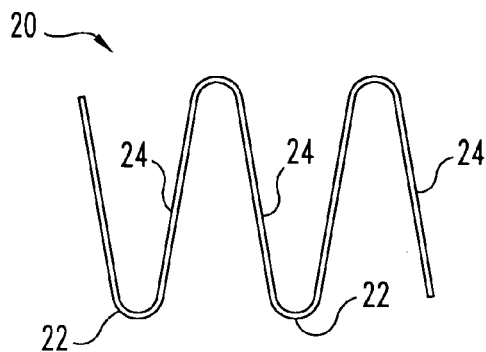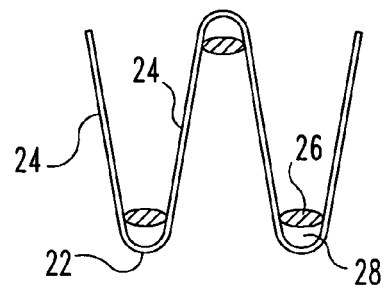
Fig. 1A    Fig. 1B
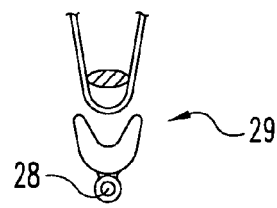
Fig. 1C
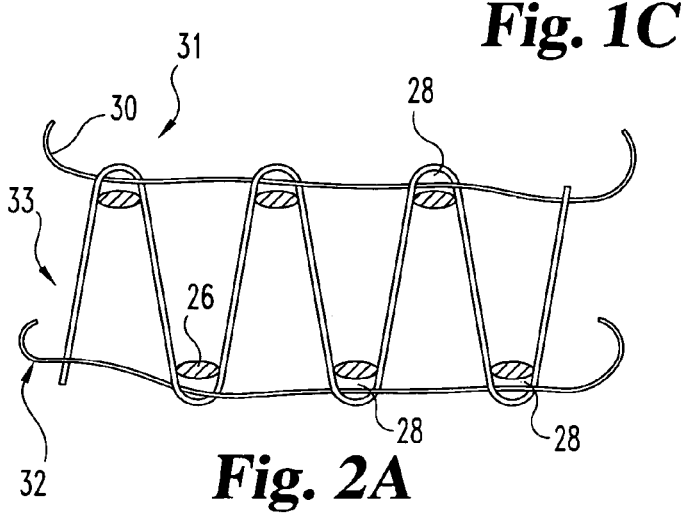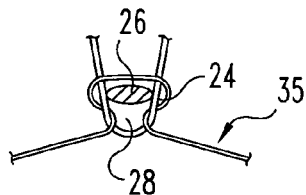
Fig. 2A    Fig. 2B
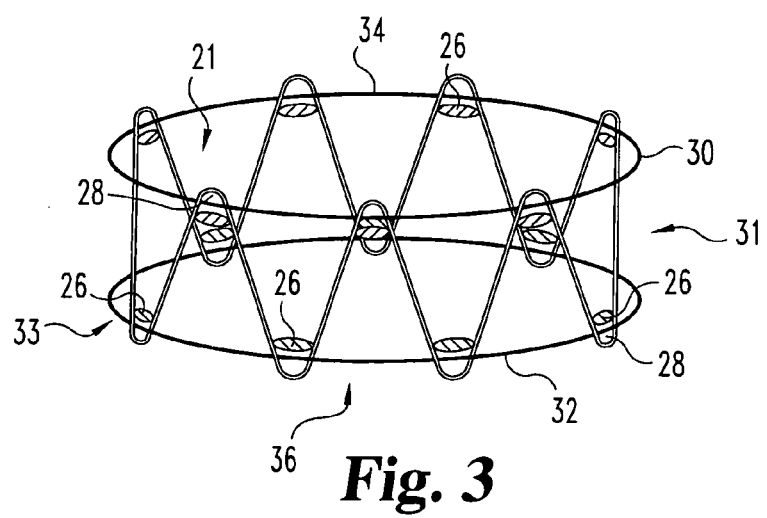
Fig. 3 ated as a national stage entry of PCT/US01/03095, filed Jan. 31, 2001, which claims priority from U.S. Provisional Application No. 60/179,195, filed Jan. 31, 2000.

STENT VALVES AND USES OF SAME

This application is a continuation of U.S. application Ser. No. 10/182,970, filed Aug. 2, 2002, now abandoned, which is a national stage entry of PCT/US01/03095, filed Jan. 31, 2001, which claims priority from U.S. Provisional Application No. 60/179,195, filed Jan. 31, 2000.

BACKGROUND

1. Technical Field of the Invention

The invention includes a medical device and more specifically to a valve found generally within a frame. In preferred devices the frame is comprised of a radially expandable stent which can be delivered through a delivery device such as a catheter.

2. Background of the Invention

Lower extremity venous hypertension in addition to venous insufficiency is a major cause of morbidity in the United States. Symptoms of venous disease include lower extremity edema, varicosities, skin pigmentation changes, skin ulceration, and general poor circulation. One solution to this problem is to replace the defective valve or the vein with a valve assembly.

Current valves include a pressure responsive, pressure directed ball movement valve assemblies. The problem with mechanical ball valves is that mechanical valves are susceptible to clot formation. Additionally, there are problems associated with long-term wear and tear on the device.

Artificial valves such as biological valves are also known. Biological valves include homografts, allografts, and xenografts. Problems associated with some biological valves include the supply of the valves, immunity response, or problems associated with matching the size with the donor.

Finally other problems associated with valve repair include placement problems in which the device cannot be repositioned once it is ejected from the placement catheter, leakage that occurs, around the valve, and emboli formation.

In light of this background, there remains a need for alternative and improved devices and methods for providing valvular function within vessels of the body. The present invention is addressed to these needs.

SUMMARY OF THE INVENTION

Disclosed is a medical device comprising a frame that has a valve generally located within. In preferred forms of the invention, the frame is comprised of a radially-expandable stent (including especially a self-expanding stent), which can be delivered through a delivery device such as a catheter, and then deployed and expanded at a target site in a body lumen such as an artery or vein. For example, in one preferred use, such a stent and method are used to treat incompetent veins in the legs or feet.

BRIEF DESCRIPTION OF THE DRAWINGS

FIGS. 1A to 3 demonstrate one embodiment of the invention comprising a stent.

DETAILED DESCRIPTION OF THE INVENTION

Figure 15:
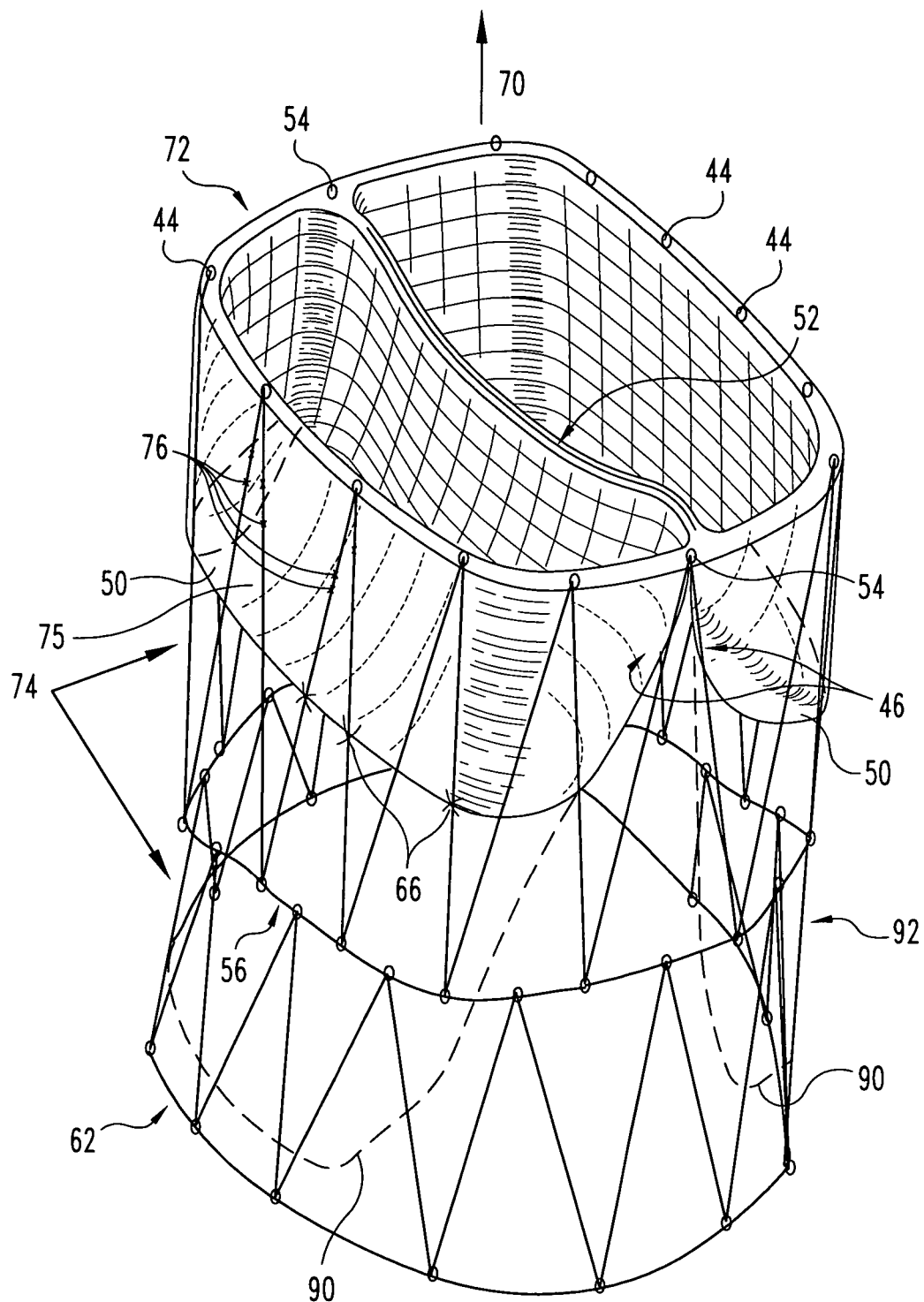

With reference to FIG. 15, shown is one embodiment of the present invention. The invention includes a frame such as a wire stent that has a lumen extending therethrough. Near one end of the stent is the valve assembly comprising some leaflets or cusps. A valve opening is generally located between the leaflets through which fluid flows. Although shown as a two leaflet valve, equally the invention can comprise, in any embodiment described herein, at least one leaflet such as two, three or four leaflets.

With respect to FIGS. 1A, 1B, and 1C, a frame is partially shown. The frame can comprise a stent 20. Choices of stent include a self expanding stent or a non-self expanding stent. In one embodiment of the present invention stent 20 is a self expanding stent such as the Gianturco stent available from Cook Inc. of Bloomington, Ind. as described in U.S. Pat. No. 4,580,568, the entire disclosure of which is expressly incorporated by reference herein. Such stent can be any length, but in one embodiment, the stent is about 15 mm long. Stent 20 includes a plurality of bends 22, which generally form the area in which the stent struts 24 reverses direction. Bends 22 are generally rounded to provide an atraumatic condition. Since the stent 20 is generally located in a vessel or body lumen of some type, the stent 20 can be cylindrical and therefore has a stent diameter 21 (shown in FIG. 3). In another embodiment, the stent 20 can also have a plurality of connectors 26 that connect adjacent struts 24. One way to provide a connector 26 is to dispose a solder bead between the adjacent struts. However connector 26 can also be a suture, weld, adhesive, rod, clamp, or other well-known ways to connect adjacent struts 24. Connector 26 provides several non-critical advantages. Connectors 26 can attach adjacent struts 24 to minimize or prevent flaring of the ends of the stent 20. Furthermore, connector 26, if placed near the bend 22, can create a hole 28 wherein the boundaries of the hole are the wires of the stent operating in general conjunction with the connector 26. This creates a hole 28 through which a thread or suture can run. However, as shown in FIG. 1C, a separate prefabricated hole can be created by separately attaching a hole assembly, such as a cap 29 over the bend 22. In any case, one benefit of the connector 26 or cap 29 is that they increase the radiographic visualization of the invention. Particularly, if the connector 26 is a solder bead, it has increased radiopacity.

With respect to FIGS. 2A and 2B, shown is part of the stent in which connector 26 attaches adjacent struts 24. As mentioned above, a thread or suture can be threaded through the hole 28. A proximal suture 30 can be sewn through the stent proximal bends 22 or stent proximal ends 31 of the stent. Similarly, a distal suture 32 can be sewn through the stent distal end 33 or the stent distal bends 22 of the stent. One way to thread the suture is shown in FIG. 2B wherein the suture 35 (generically any suture) runs over the strut 24 to enter the hole 28, through hole 28 to come behind the same strut 24, over the strut 24 and across to the adjacent strut 24 running over the adjacent strut 24, behind the adjacent strut 24 to come from behind and through hole 28, and then run subsequently over adjacent strut 24. Once the struts are connected via the suture, the suture can be pulled to a predetermined tightness to control the overall stent size. Accordingly, the stent can be so constructed to have a predetermined stent perimeter 34. To this end, the stent lumen 36 will also have an appropriate size.

The stent can be constructed so as to have a different perimeter length at the proximal or distal ends.

With regard to FIG. 3, shown is a cylindrical stent 20 that has the proximal and distal sutures running through the bends 22 or holes 28 of the proximal and distal ends of the stent. By altering the tautness of the sutures, the size of the stent lumen 36, the stent diameter 86, and the stent perimeters 34, can be adjusted. As can be seen, distal perimeter suture 32 runs along the stent distal end 33, whereas proximal perimeter suture 30 runs along the stent proximal end 31. The respective sutures run through hole 28 of each bend 22.

Figure 4:
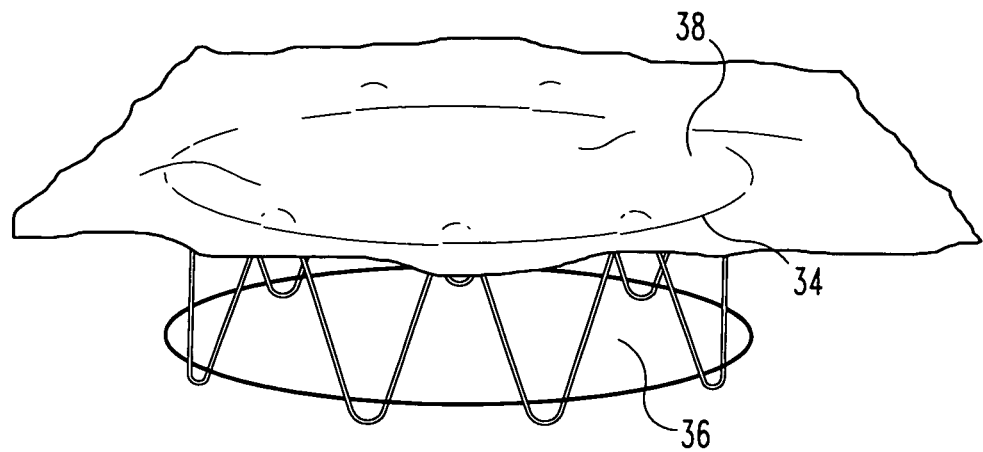
FIGS. 4 to 8 demonstrate other embodiments of the present invention comprising the valve.
Figure 5:
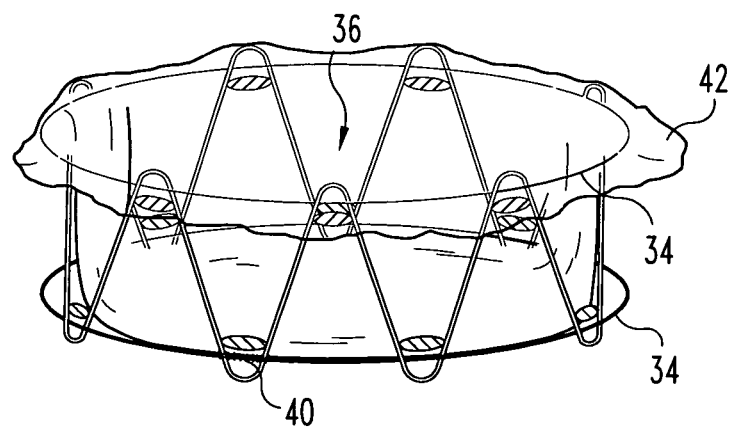

With respect to FIGS. 4 and 5, the valve material 38 is shown, in this exemplary embodiment, as a sheet. In so constructing the valve 41, the valve material 38 is draped across the stent lumen 36 opening (such as shown on the proximal portion of the stent) and then pushed down into the stent lumen 36 itself. Excess material can be kept outside the stent, which will later become a potential fold-over 42. However, the excess material can also be trimmed off. The valve material 38 is connected to the stent, using for example, distal valve-stent suture 40. However, any well known ways to connect the valve to the stent is contemplated, such as but not limited to, sutures, adhesives, folds, or the like. In one embodiment shown in FIG. 5, the valve-stent suture 40 can share the hole 28 with distal suture 32 near the stent perimeter 34.

The valve material 38 can be any biocompatible material such as polyethylene terephalate(PET), polypropylene(PP), polytetrafluorethylene(PTFE), or any polymer or derivative thereof, and also includes commercially known materials such as GORE-TEX, DACRON, or any other synthetic material. The preferred material 38 will be advantageously compliant and employed so as to permit effective value function as described herein and in the case of collapsible/expandable state devices will retain integrity and function when cycled between these states.

It is preferred to use a biomaterial that serves as a biocompatible scaffold with the ability to remodel host tissue. Accordingly, a naturally occurring biomaterial is highly desirable. One such biomaterial is collagen and more particularly, a collagen based biomaterial called extracellular matrix (ECM). Examples of ECM's include pericardium, stomach submucosa, liver basement membrane, urinary bladder submucosa, tissue mucosa, dura mater, and small intestine submucosa One such biomaterial is the ECM, such as submucosa, and more particularly is small intestine submucosa (SIS). SIS can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated May 28, 1998, which is the published application of PCT/US97/14855; Gastric Submucosa as described in WO 98/26291 (PCT/US97/22729), claiming priority to U.S. Provisional application No. 60/032, 686; Liver tissue as described in WO 98/25637 (PCT/US97/22727), claiming priority to 60/032,680; Stomach Submucosa as described in WO 98/25636 (PCT/US97/23010), claiming priority to 60/032,683; and Urinary Bladder Submucosa as described in U.S. Pat. No. 5,554,389; all the disclosures of which are hereby expressly incorporated by reference. Irrespective of the origin of the valve material (synthetic versus naturally occurring), the valve material can be made thicker by making multilaminate constructs, for example SIS constructs as described in U.S. Pat. Nos. 5,968, 096; 5,955,110; 5,885,619; and 5,711,969; the disclosures of which are entirely and expressly incorporated by reference.

Figure 6A:
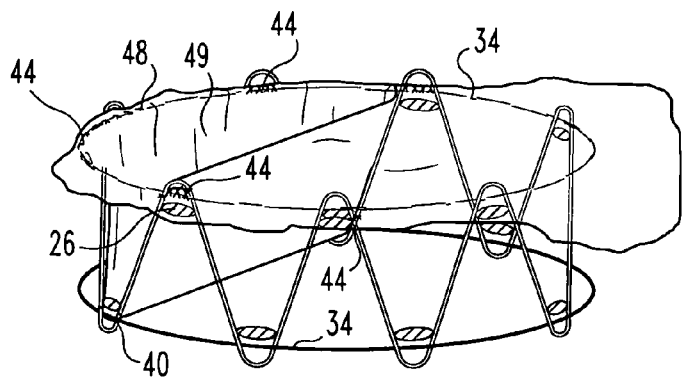
Figure 6B:
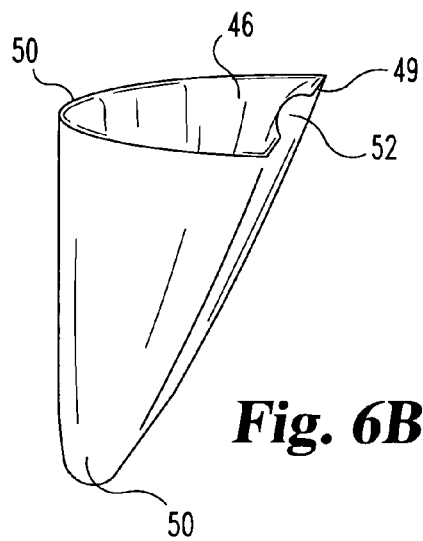

With respect to FIGS. 6A and 6B, shown is the connection of the valve to the stent frame. As described above, the valve can be sutured at the distal portion of the stent using distal valve-stent suture 40. Similarly, the proximal portion of the valve can be sutured to proximal portion of the stent, and more particularly to proximal perimeter suture 30. Shown is the valve connected to the proximal portion of the stent at proximal valve-stent suture 44. Suture 44 can be through a bend 22 or can attach to the proximal perimeter suture 30. In a traditional Gianturco Z-stent, it is either an 8 (bend) point or 10 (bend) point stent, so one leaflet of the valve can be sutured to the four points of an 8 point stent thereby comprising one half of the stent. To provide further integrity, the valve can be sutured at the proximal and distal end to the perimeter sutures themselves, without actually being sutured to any or all of the stent bends 22.

With respect to FIG. 6B, shown is the valve with the stent frame removed. Once the sutures are generally in place, the valve sheet 38 will form a valve pocket 46, extending inside the stent lumen in which the fluid will fill. Proximal valve perimeter 48 will have the sutures connecting the valve to the stent (not shown). Once the distal sutures are in place, the general shape will likely resemble a pocket with the pocket having a valve apex 50. There is a part of the valve that will form central valve portion 49 that is not directly sutured to the stent. This valve portion 49 will form the valve opening 52 through which fluid will pass. Thus, upon filling of the valve pocket 46, the fluid pressure will exert outwards causing valve portion 49 to extend outward. When it does, it will contact the other leaflets or cusps and form a seal to stop or impede fluid flow.

Figure 7:
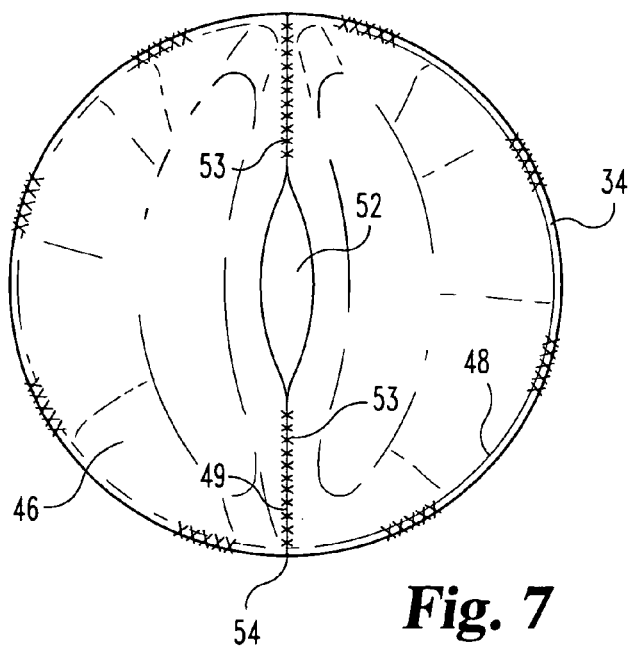

FIG. 7 shows a top view of the stent valve. In this particular non-limiting view, shown is the valve opening 52 in a slightly open configuration. Valve pockets 46 are shown in a slightly distended configuration. The valve is connected, for example, by sutures to the stent perimeter 34 and also forms a valve perimeter 48. Because of the opening and closing of the valve, there may be increased wear and tear at the valve-stent-opening connection. At this point, one embodiment of the present invention provides a reinforcement at this point. For example, this reinforcement can be a plurality of reinforcement sutures 54, adhesive, another material, or any other mechanism that permits increased structural integrity.

Figure 8:
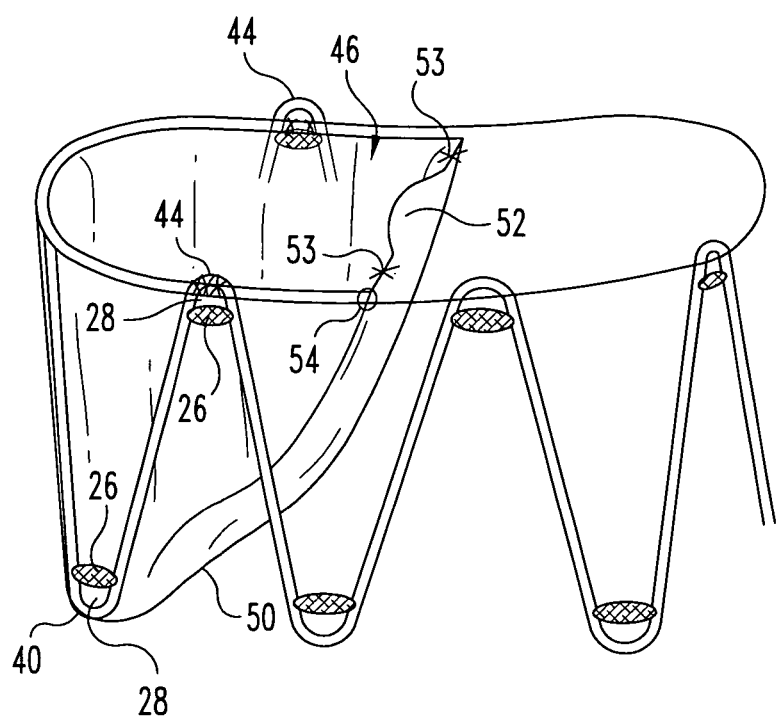

FIG. 8 demonstrates a view of the stent valve once the distal portion of the valve is sewn to a distal bend 22 and also shows the proximal portion of the valve being connected to the proximal portion of the frame with one suture in the foreground, one suture in the background. In addition, the reinforcement suture 54 is found in the foreground. Although only two sutures 44 are seen at the proximal portion, it is of course well-understood that some or each of the proximal bend of the frame can be connected to the proximal portion of the valve. Similarly, although only one distal suture 40 is shown, there may be as many distal sutures necessary to connect the valve apex 50 or the distal portion of the valve to the frame. It is well understood that this may be just one distal suture or many distal sutures. Varying the number of distal sutures will vary the shape, tightness, and overall configuration of the valve, valve pocket 46, and the valve apex 50.

The valve opening 52 although already described above, is actually created in the final step of preparation of the preferred device manufacture. The construction mentioned above would be repeated on the other side of the valve to create the valve pocket 46, valve apex 50, and the like on the other side. At this point, though, there is no valve opening 52. The valve opening 52 is created by creating a slit in the sheet to create the opening. The slit can be sized according to the intended flow rate of the passing fluid. Accordingly, a large slit would create a large valve opening or orifice and permits a large volume of fluid to pass therethrough. The slit can be created by poking a scalpel through it and running it to the desired length. However, due to potential fatigue at the orifice, another set of reinforcements may be added to the orifice perimeter. Therefore, as shown in FIGS. 7 and 8, an orifice reinforcement 53 may be created by any known conventional ways, such as sutures (resorbable or non-resorbable), adhesive, string, staples, rings, or the like.

Therefore, the stent valve as constructed can be using one stent with the valve material enclosed therein. Of course in the single stent configuration, the overall length can be adjusted by elongating the length of the struts 24. However, devices of the invention can be built using a plurality of stents to elongate the overall size of the stent, if desired. In this regard, it will be preferred that the length of the device 20 is sufficient to provide an aspect ratio (length to expanded diameter) sufficiently high to facilitate proper alignment of the device 20 within the vessel, with the axis of the device lumen generally aligned with the axis of the vessel. For example, devices having a ratio of length:expanded diameter of 1:1 or greater, or about 2:1 or greater, will be preferred. It will be understood that while such dimensions will advantageously facilitate placement of the inventive devices, they are not necessary to the broader aspects of the invention.

Figure 17:
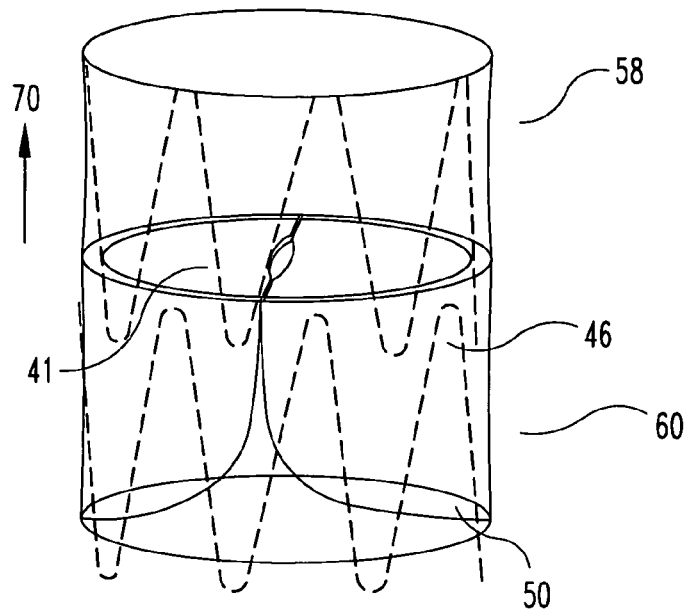
FIGS. 17 to 19 demonstrate other alternative embodiments.
Figure 18:
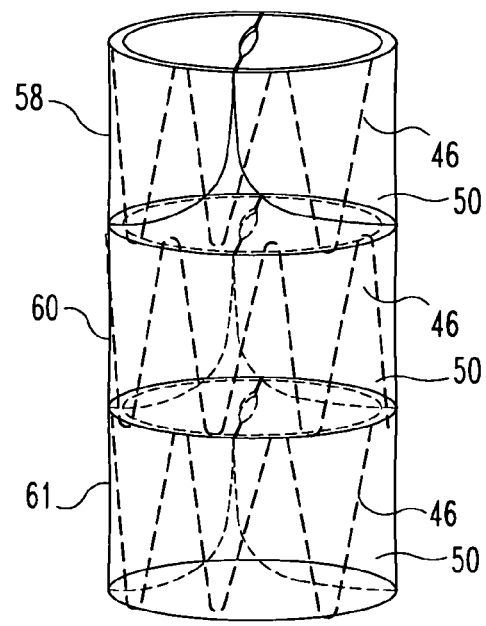
Figure 19:
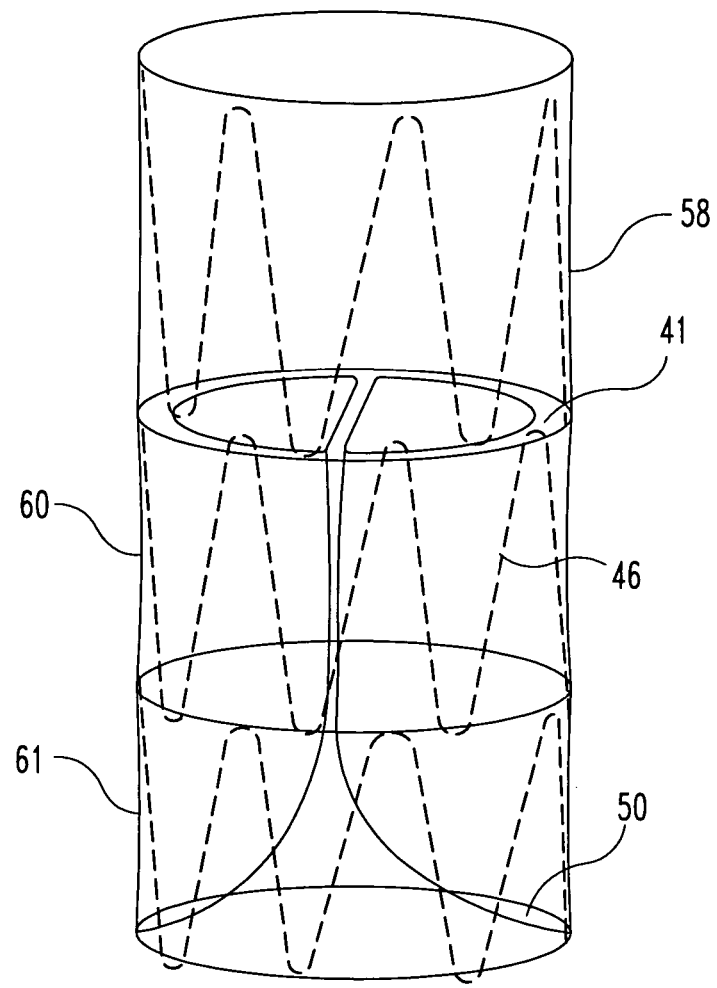

With reference to FIG. 15, shown is a double stent structure with the valve. Returning now to FIG. 9, shown is a first stent 58 and a second stent 60. For the purposes of discussion only, first stent 58 is shown to be atop of the second stent 60. Ultimately as shown herein by way of example only, the valve will reside in the first stent 58. It should be noted however that the valve can reside in the second stent 60 also as shown in FIG. 17. Furthermore, the overall length can be increased by joining several stent valves together as shown in FIGS. 18 and 19, thereby having a plurality of stents, such as a first stent 58, second stent 60, and a third stent 61. The valve 41 can be placed in any or all stents, in any combination, for example, as shown by the dotted lines. In this regard, it is suggested and intended that many stents can be joined and that each or any stent may house a valve or plurality of valves. One benefit of having a plurality of stents is that upon ejection of the placement device, the invention will provide a self-aligning feature in the vessel. This is because the plurality of stents is generally longer with respect to the stent diameter, or the plurality of valve device(s), as discussed above.

Manufacture of the multi-stent or multi-valve device will generally follow the same construction as described above. The same considerations in making a single valve single stent device applies equally to the elongated device.

Figure 9:
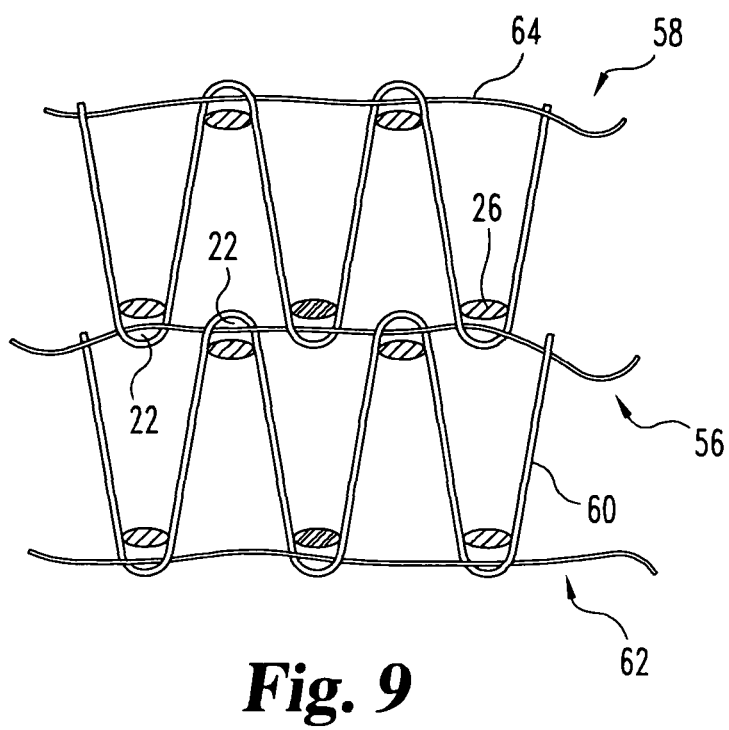
FIGS. 9 to 11 demonstrate embodiments that illustrate exemplary ways of attaching a plurality of stents.
Figure 10:
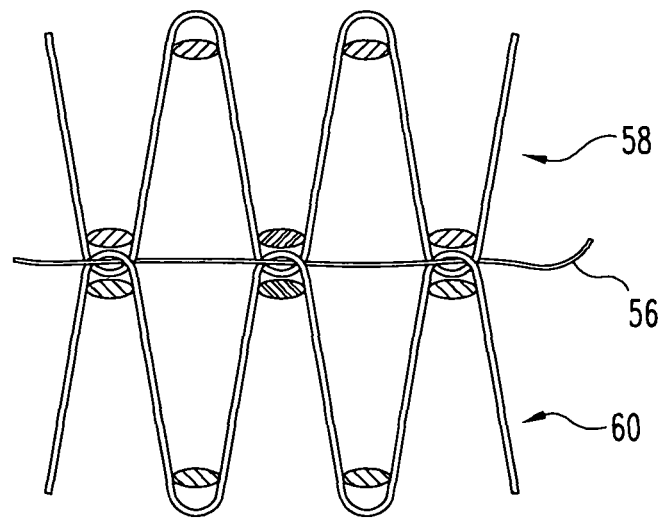

Returning now to FIGS. 9 and 10, shown are methods of connecting the first stent 58 and second stent 60. Equally, the construction shown from now on also includes construction of at least two stents or at least two valves. First stent 58 and second stent 60 has bends 22 that are adjacent each other. Shown in FIG. 9 is where the first stent 58 has its bends beside the bends of the second stent 60 such that they are not touching each other (although they may touch). They are connected together in the manner described above, and for example by stent-stent suture 56. Stent-stent suture 56 can be resorbable or non-resorbable. This suture travels through the distal bends of the first stent 56 and the proximal bends of the second stent 60. The suturing pattern can be that described in FIG. 2B and the accompanying discussion. As shown in FIG. 10, the bends can be juxtaposed over each other to provide an overlap such that the stent-stent suture 56 will go through the bends at the same time. Therefore, the construction contemplates that the stent bends may touch, overlap, or not at all.

Figure 11:
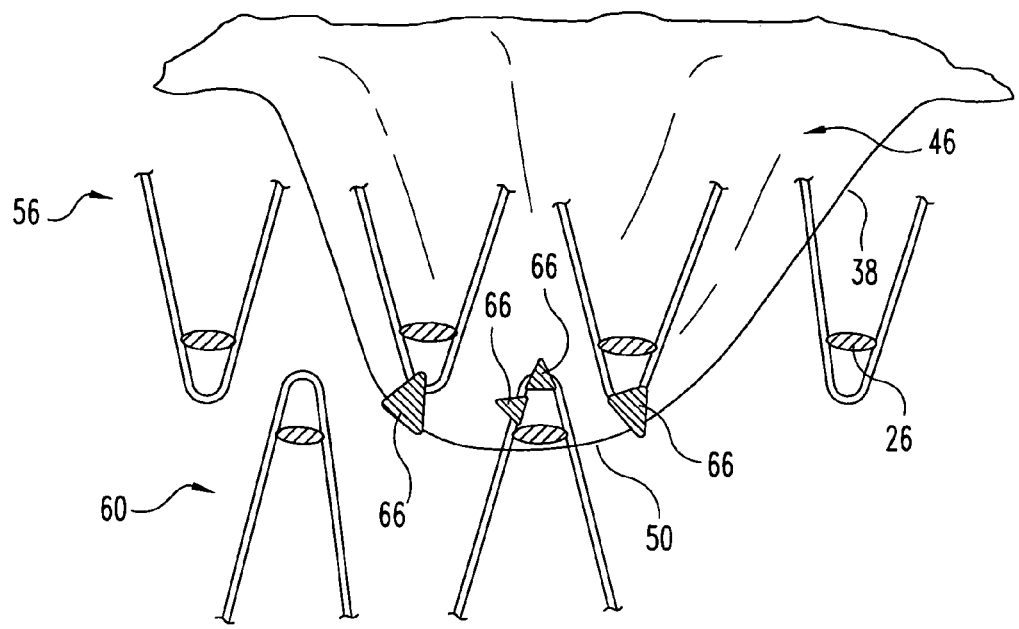

FIG. 11 shows one embodiment of the present invention in which the valve apex 50 is sutured to at least three bends: two bends of the first stent 56 and one bend of the second stent 60. In this regard, the valve also operates to keep the first stent 56 partially connected to the second stent 60. From the bends, a plurality of valve apex sutures 66 are seen. These sutures can emanate from the bends and each bend can have many valve apex sutures 66 that travel in many directions. Using multiple valve apex sutures 66 that emanate in many directions and using a plurality of bends (from either stent), generally functions to minimize any parachuting or inversion of the valve pocket 46.

Figure 12:
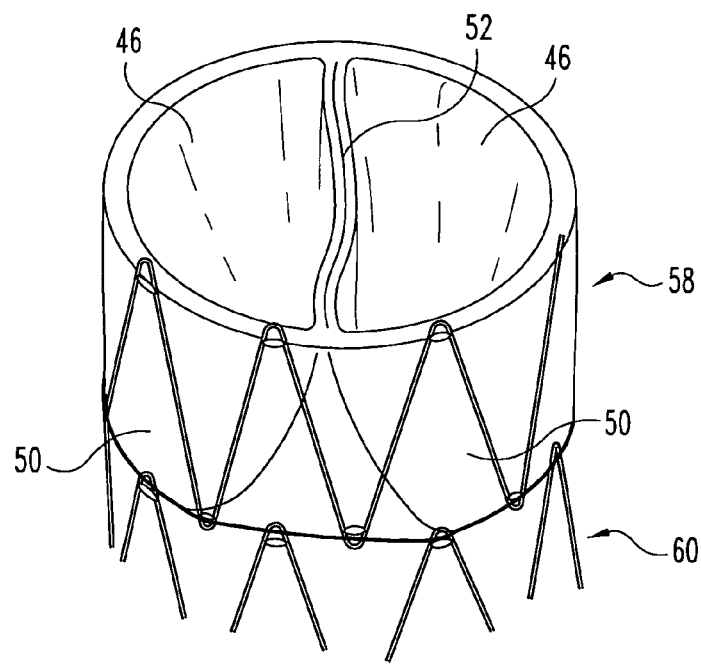
FIGS. 12 to 15 demonstrate exemplary embodiments of the valve configuration in a variety of stent embodiments.

FIG. 12 demonstrates a top view of the multi-stent device in which the valve opening 52 is seen (in a closed position) and the valve pocket 46 and valve apex 50 is connected to three bends. Again it should be understood that many sutures may emanate from many bends from any stent.

Figure 13A:
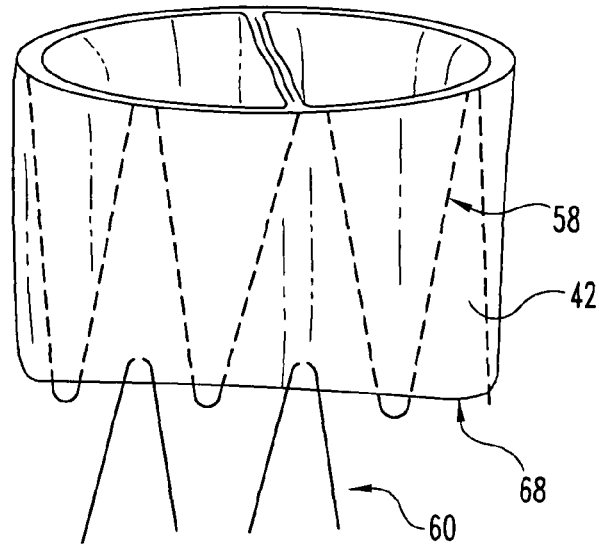
Figure 13B:
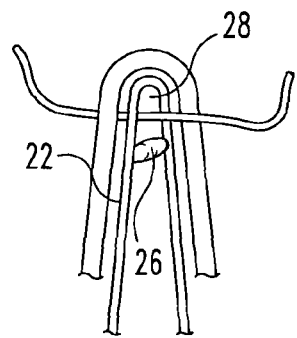

As described earlier, the excess material can either be trimmed off or folded over the outer surface of the device. Shown in FIGS. 13A and 13B, is the excess material being folded over the device and attached at the distal end of the first stent 58. Shown in dotted lines is the first stent 58. FIG. 13B shows that the fold-over 42 provides a second material outer sheath so that the suture passes through the inside and outside material to increase structural integrity. Also, by folding over the excess material, a smoother surface is presented rather than the naked frame of the tip of the bend.

In all embodiments of the invention, the external surface of the frame can be covered with a sheath that is not necessarily the same material as the valve 41. For example, while the valve can be a naturally occurring material, the outer sheath can be synthetic material such as described herein. The sheath, therefore, can be the fold-over of the valve material, another type of naturally occurring material, or a synthetic material. Accordingly, the sheath may partially or totally cover the frame.

Figure 14:
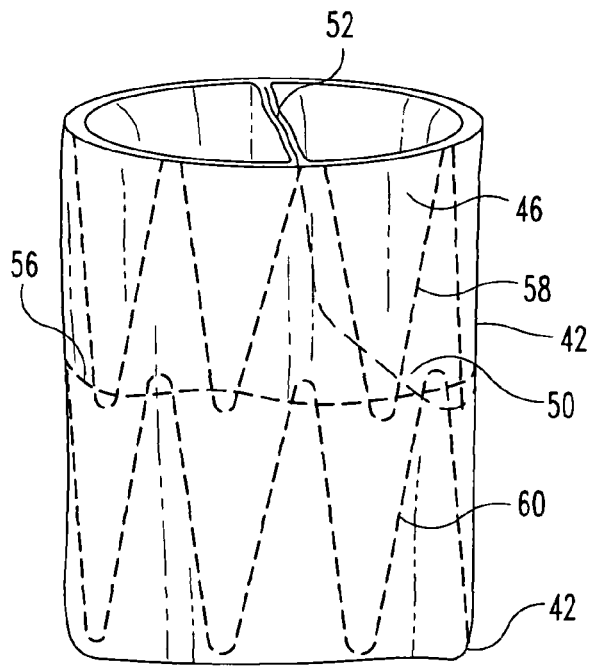

FIG. 14 shows an embodiment in which both the first stent 58 and second stent 60 are covered by the fold over 42. Here, the fold-over 42 is connected to the distal portion of the second stent 60. In this manner, the entire device may be covered with an outer sheath of biomaterial. The benefit of doing so, especially if using SIS or other similar ECMs, is that the regrowth and endothelialization of the device embeds and encapsulates the frame. Accordingly, there is a reduced risk of device migration. Furthermore, due to the remarkable remodeling properties of SIS, the outer SIS sheath acts as a conduit for host tissue to infiltrate the device and remodel the valve itself. Over the course of months, the valves are replaced by host tissue and the SIS disappears.

FIG. 15 shows yet another embodiment of the present invention. In this demonstration, the valve is located in the first stent 58, sutured at the proximal end at the stent perimeter. The valve apex 50 is sewn somewhat proximal of the stent-stent suture 56. The valve apex 50 is sewn at the valve apex sutures 66 to an intermediate portion of the frame. To minimize parachuting or inversion, a valve intermediate portion 75 may be sutured using valve intermediate suture 76 to connect the valve to the frame. In addition, the valve may be so constructed to extend the valve's length to create an elongated valve pocket 90 (shown by the dotted lines). While the extended pocket 90 can be connected to the distal perimeter of the second stent distal suture 62, it can also be connected to an intermediate portion of the second stent.

With further reference to FIG. 15, it is seen that the valve opening 52 is a slit that extends across the first stent diameter 21 but terminates several millimeters before reaching the edge. In some embodiments, this distance could be 1-5 mm from the edge. Of course, it is understood that the invention contemplates any distance that varies the length of the slit. Also, shown in FIG. 15, but equally applies to any device described herein, is an anchor 92, which can be anchor barbs 92. These barbs 92 can dig into the adjacent vessel wall to relatively affix the device at its location. Anchor 92, although shown as barbs, may include hooks, adhesives, knobs, a textured surface, or any other treated surface that facilitates relative affixation of the device in its location. Similarly, the outer surface of the fold-over or sheath can be so configured to provide anchoring.

Figure 16:
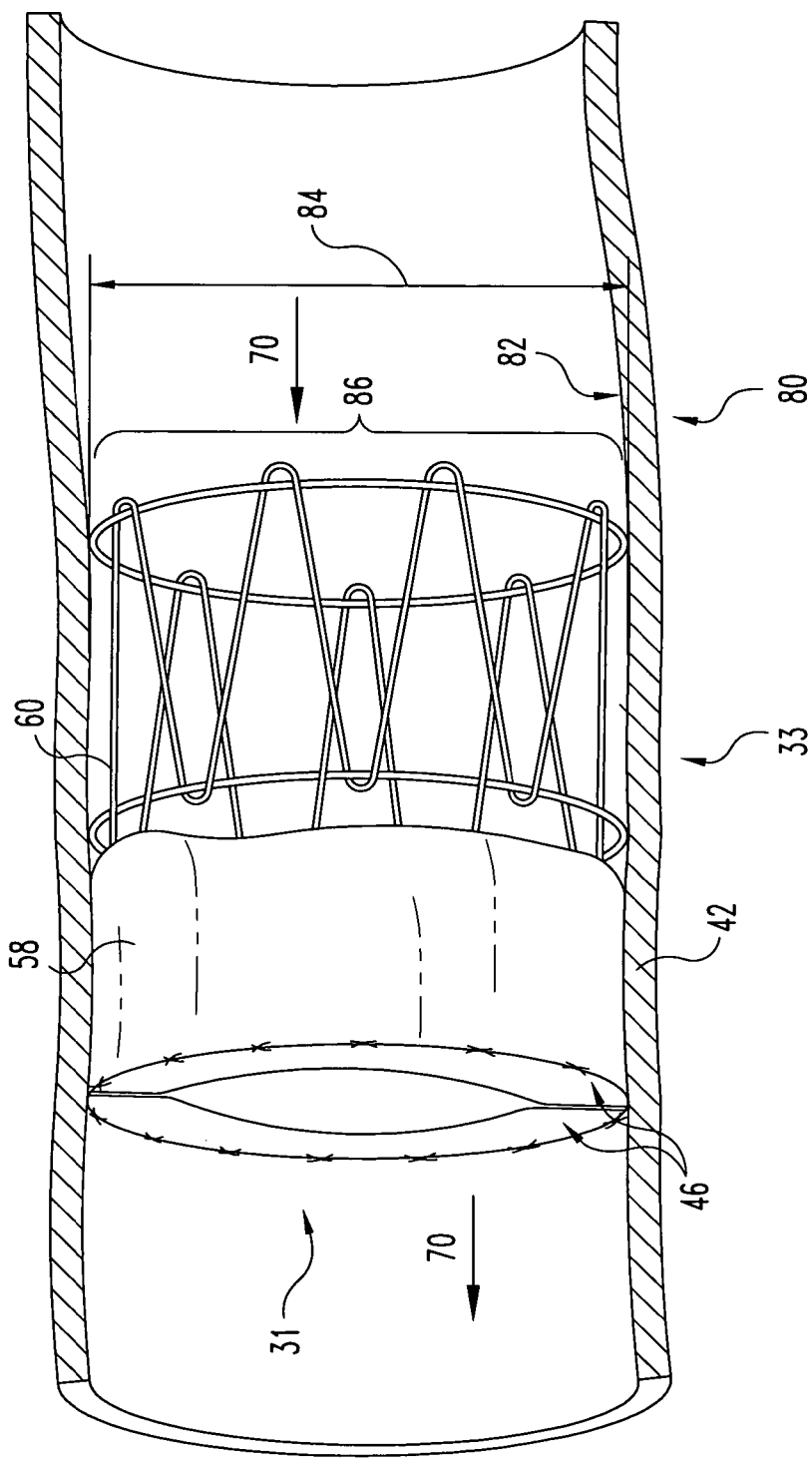
FIG. 16 demonstrates one aspect of the invention in situ.

FIG. 16 demonstrates the device upon implantation into the patient. Upon implantation the device generally resides in a vessel 80. For example, the vessel could be vein, artery or the heart or wherever a valve is necessary. In one preferred use, the vessel is an incompetent vein in the leg or foot of a patient. The device 20 reduces or prevents retrograde blood flow, while normal blood flow is permitted to travel through device 20. Illustrative veins in which the device 20 may be used include, for example, saphenous veins, femoral veins, popliteal veins, tibial veins, and the inferior vena cava.

The vessel 80 has an inner lumenal surface 82 in which the fluid flows. The fluid flow path is shown as fluid path 70. Vessel 80 also has a vessel diameter 84. The medical device, upon implantation, will also have a device outer stent diameter 86. The outer diameter 86 will be chosen to permit contact with the inner lumenal surface 82. The optimized fit will decrease the leakage around the device by contacting the inner lumenal surface 82. A tight fit can be accomplished by sizing the stent diameter to be greater than the vessel diameter. For example, a stent diameter that is about 110 percent greater than (i.e. 1.1 times) the vessel diameter provides a good fit. Expanded stent diameters of about 10 mm to about 30 mm will be typical in many applications of the present invention. Again, while it is shown in this FIG. 16 that the valve is located in the first stent 58 and only the first stent 58 is covered by the fold-over 42 or sheath, it should be remembered that the valve could be located in the second stent 60. Similarly, the fold-over 42 or sheath could extend onto the second stent 60.

Figure 20:
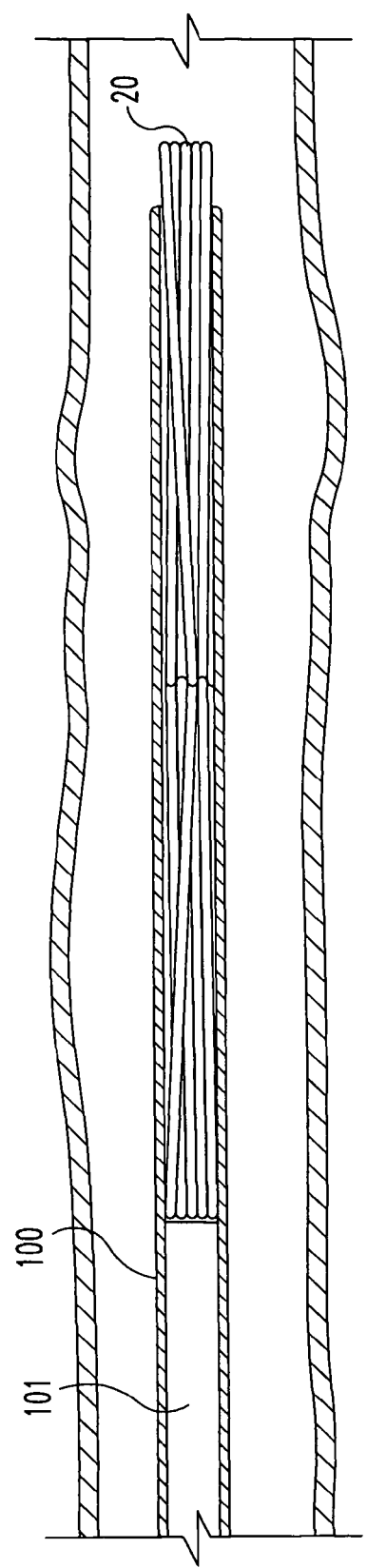
FIG. 20 depicts a medical assembly of the invention including a stent valve and a delivery device for the stent valve.

The standard method of deploying the medical device 20 in a vessel 80 involves the use of a medical assembly (see FIG. 20) including the device 20 and a delivery device such as a percutaneous delivery device, e.g. a catheter 100. The frame is configured to a contracted state, e.g. by resiliently forming the frame into a contracted configuration, to load into the delivery device (catheter). The catheter can be introduced into the patient via a suitable approach, for example through the jugular or femoral vein. To advance and deploy the device from the distal end of the delivery catheter, a pusher 101 is placed into the catheter lumen. When the device 20 is fully deployed, it assumes the second, expanded configuration within the vessel 80 as depicted in FIG. 16. The stent frame, being made of resilient material, conforms to the shape of the vessel wall such that when viewed on end, the device 20 has a circular appearance when deployed in a round vessel.

FIGS. 17, 18, and 19 show other described embodiments. FIG. 17 demonstrates the valve 41 in the second stent 60. In this embodiment, the valve apex 50 is connected to the second stent's distal perimeter. FIG. 18 demonstrates at least two stent frames connected together. In this particular embodiment, the valve is located in the first stent 58, with the valve apex 50 being connected at the first stent 58-second stent 60 junction. In dotted lines, however, there may be many stents, such as first stent 58, second stent 60, and third stent 61. The valve 41 may be found in any of the stents or in all. Similarly, in the three stent configuration, the valve may begin at the first stent and have the valve apex 50 be generally located in the third stent 61. FIG. 19 shows another embodiment of the present invention in which the valve 41 begins in the second stent 60 and extends into the third stent 61 thereby having the first stent 58 being empty.

Finally, since the device is located in an in vivo environment, the device may be treated with therapeutic agents to facilitate healing. For example, the frame may be treated with therapeutic agents such as anticancer drugs, plaque busters, anti-coagulants, or the like. Similarly, the valve material can be treated with therapeutics agents such as anti-cancer drugs, plaque busters, anti-coagulants, proteins, growth factors, proteoglycans, and the like. Furthermore, radiopaque agents may be added, such as tantalum, barium, bismuth, or the like to increase radiopacity. These ingredients can be bonded to the frame or the valve material such as rubbing the agent in, bonding it, adhering it, or the like.

While the invention has been illustrated and described in detail in the drawings and the foregoing text, it is understood that these are only some embodiments and that the scope of the invention is not solely defined by the description herein but also by the appended claims. All modifications and changes that come within the spirit of the invention are hereby protected.

What is claimed is:

1. A percutaneously implantable vascular stent valve device, comprising:
   a percutaneously implantable frame having a longitudinal axis and an inner lumen;
   a valve connected to the frame and comprising two or more flexible leaflets located at least partially within the frame, the two or more leaflets defining a valve orifice between upper portions of the leaflets which extend across the lumen of the stent and have inner segments that are moveable into and out of contact with one another to close and open the valve orifice, respectively; and
   wherein said upper portions of adjacent leaflets of the two or more leaflets have respective peripheral segments that are positioned inside the frame and that are sewn together by a linear series of suture stitches to create sewn-closed leaflet material segments inside the frame and between an inner surface of the frame and said inner segments, said sewn-closed leaflet material segments extending transverse to said longitudinal axis and said sewn-closed leaflet material segments occurring immediately adjacent to and defining an outer periphery of the valve orifice, with said sewn-closed leaflet material segments contributing to a reinforced connection of the leaflets to the frame.

2. The valve device of claim 1, wherein:
   the valve orifice has orifice termini spaced inward of the inner surface of the frame by a distance of about 1 to 5 mm.

3. The valve device of claim 1, wherein the frame is a self-expanding frame.

4. The valve device of claim 1, wherein the frame is a non-self-expanding frame.

5. The valve device of claim 1, wherein the two or more flexible valve leaflets comprise collagen.

6. The valve device of claim 5, wherein the two or more flexible valve leaflets comprise a material selected from the group consisting of pericardium, submucosa, and dura mater.

7. The valve device of claim 5, wherein the two or more flexible valve leaflets comprise submucosa.

8. The valve device of claim 5, wherein the two or more flexible valve leaflets comprise pericardium.

9. The valve device of claim 1, which is a vein valve device.

10. The valve device of claim 1, which is a heart valve device.

11. The valve device of claim 1, wherein the frame comprises a radially expandable stent.

12. The valve device of claim 1, wherein the frame has a first end with a first perimeter length, and a second end with a second perimeter length, and wherein the first perimeter length differs from the second perimeter length.

\* \* \* \* \*